United States Patent [19]

Smith

[11] Patent Number: 5,042,476
[45] Date of Patent: Aug. 27, 1991

[54] ENDOTRACHEAL TUBE PROTECTION ARRANGEMENT

[76] Inventor: Charles A. Smith, 811 Starlite Dr., Louisville, Ky. 40207

[21] Appl. No.: 392,016

[22] Filed: Aug. 10, 1989

[51] Int. Cl.$^5$ .......................................... A61M 16/00
[52] U.S. Cl. ........................... 128/207.14; 128/207.15
[58] Field of Search ....................... 128/207.14, 207.15, 128/200.26

[56] References Cited

U.S. PATENT DOCUMENTS

| | | | |
|---|---|---|---|
| 3,348,542 | 10/1967 | Jackson | 128/207.15 |
| 3,766,927 | 10/1973 | Jackson | 128/207.15 |
| 4,141,364 | 2/1979 | Shultze | 128/207.15 |
| 4,378,796 | 4/1983 | Milhaud | 128/207.15 |
| 4,417,576 | 11/1983 | Baran | 128/207.15 |
| 4,423,725 | 1/1984 | Baran et al. | 128/207.15 |
| 4,489,722 | 12/1984 | Ferraro et al. | 128/207.15 |
| 4,558,093 | 12/1985 | Hatzenbuhler et al. | 128/207.15 |
| 4,632,108 | 12/1986 | Geil | 128/207.15 |
| 4,834,087 | 5/1989 | Coleman et al. | 128/207.15 |

Primary Examiner—Aaron J. Lewis
Attorney, Agent, or Firm—Kinzer, Plyer, Dorn, McEachran & Jambor

[57] ABSTRACT

A sheathing arrangement to protect an endotracheal tube from being ignited and/or punctured by a laser during surgical procedures where the endotracheal tube includes an inlet to receive anesthesia/oxygen mixture to be supplied to a patient undergoing the surgical procedure and an outlet which extends into the airway of the patient where an expandable seal is provided on the endotracheal tube to seal off the breathing passageway during the procedure and where a second flexible tubular sheath is provided to extend, be sealed around the endotracheal tube adjacent the outlet and extend upwardly substantially the length of endotracheal tube to define an annular area between the tubular sheath and the endotracheal tube where a nonflammable fluid is supplied to the annular area.

10 Claims, 1 Drawing Sheet

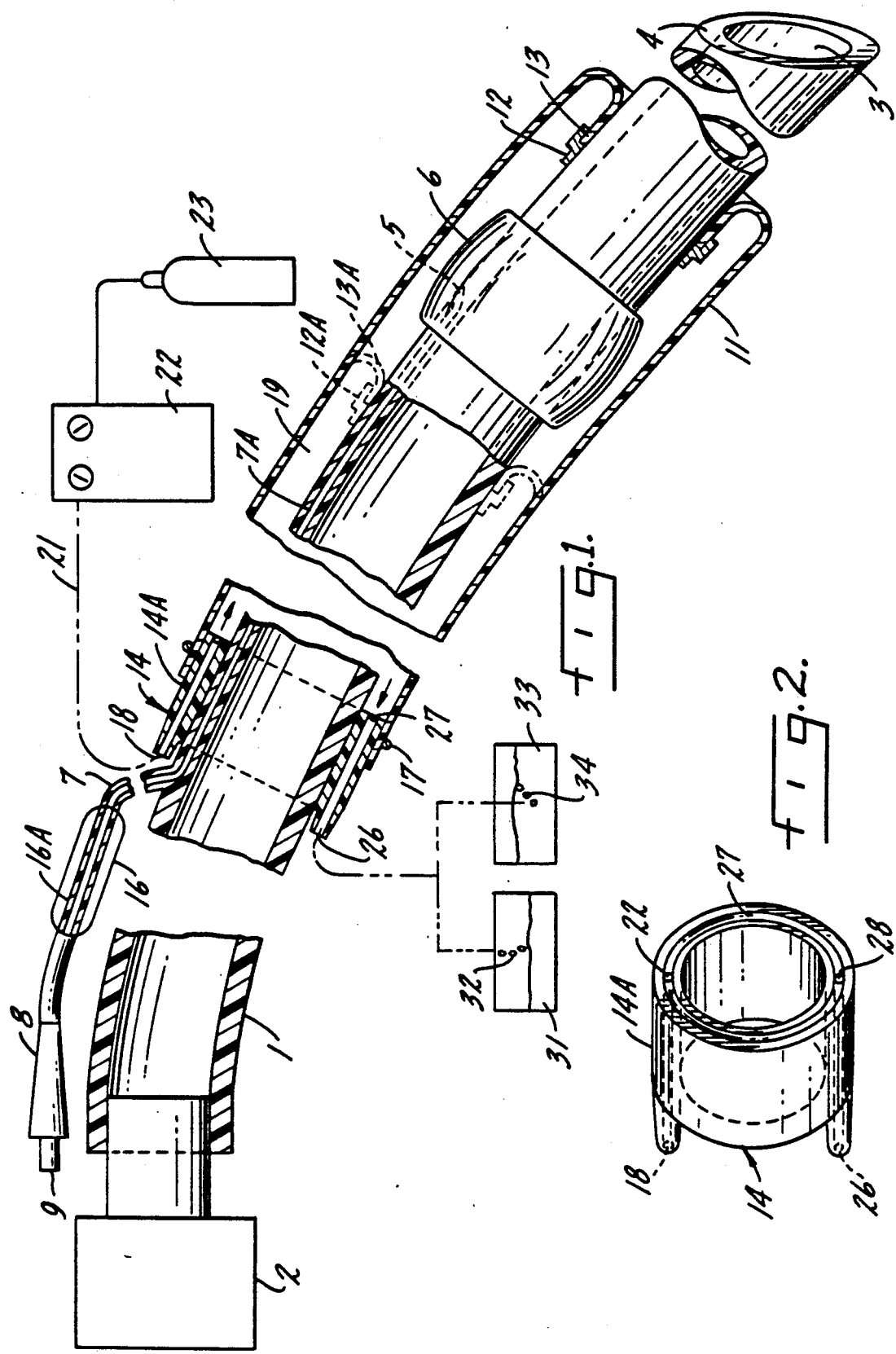

ENDOTRACHEAL TUBE PROTECTION ARRANGEMENT

BACKGROUND OF THE INVENTION

Oral endotracheal tubes are used by anesthetists to administer oxygen/anesthesia mixtures to a patient during a surgical procedure involving the throat, the larynx, or other similar locations which are normally reached by the surgeon through the mouth of the patient.

Endotracheal tubes have commonly been used for various types of surgery including ordinary surgical procedures and more recently surgical procedures using a laser surgical instrument for example a $CO_2$ laser device. However, soon after the introduction of the laser to otolaryngology, a branch of medicine dealing with the throat, nose, and ears, reports of the combustion of the flammable material of endotracheal tubes during $CO_2$ laser endoscopic surgery in the proximity to the airway began to appear. Subsequently, the combined flammabilty of the anesthetic/oxygen mixture coupled with the ability of the $CO_2$ laser to ignite the material of the tube and initiate combustion which is greatly intensified by the highly flammable gases present have been resent, reported.

Various techniques and products have been utilized to address the problem including wrapping the tube with metallic foils. However, the use of a metalic foil wrapping introduces several problems including the fact that it is difficult to maintain the wrapping and simultaneously achieve desired flexibility of the tube. Additionally, metallic foil wrapping provides an another hazard by creating a reflective surface for the laser and reflection of the laser beam from the foil wrapped tube can cause unintentional damage to tissue surrounding the area being operated on, which is not anticipated by the procedure and/or operator (surgeon). Experimentation has been carried out with various inhaled gas mixture with the intention of mixtures preventing the ignition of the combustible anesthesic/oxygen mixture with little, or no, known success, as $O_2$ in life supporting concentrations must always be present.

$CO_2$ laser otolaryngological surgery offers significant advantages over prior surgical means but to date no method or apparatus is known which successfully eliminates or diminishes the possibility of fire and disaster occurring if the laser beam contacts and/or penetrates to the combustible material of the endotracheal tube during the procedure.

The endotracheal tube is constructed of highly flammable material usually PVC or rubber. When a laser beam contacts the tube even for a short period of time, a small area of the tube receives a high level of energy which can melt and/or ignite the tube material, and aided by oxygen concentrations usually near 100% inside the tube, results in a fire that is nearly impossible to extinguish with usually catastrophic results for the patient. Surgeons and anesthesiologists report a large number of near miss occurances (about 50%) where the tube was beginning to melt but had not yet flashed into a fire from laser contact.

SUMMARY OF THE INVENTION

The present invention provides a new, useful, and effective apparatus and method for the prevention of fires, burns, and other damage during otolaryngological surgery using a endotracheal tube and $CO_2$ laser surgical instrument.

Devices within the scope of the present invention recognize that by wrapping an endotracheal tube with a reflective material to prevent intrusion of the laser beam into the endotracheal tube is in many applications unsatisfactory because of the potential damage caused by the reflected laser beam to surrounding tissue. The methods and devices within the scope of the present invention are inexpensive yet quite effective and permit the use of currently available endotracheal tubes without redesign or modification of the devices themselves, with only a few additional steps in the manufacturing procedures required for the manufacture of the devices.

Moreover, devices within the scope of the present invention provide the added advantage that the combustible breathing mixture carried inside the endotracheal tube is completely surrounded by a noncombustible fluid. Further, an outer protective envelope is provided so that a laser beam which would otherwise strike the endotracheal tube first strikes the outer protective envelope which holds the nonfammable fluid. However, in the event the endotracheal tube itself is struck/or pierced by the laser beam the area of puncture, which is where combustion would occur, is surrounded by the noncombustible fluid so that any combustion, which may occur is quickly extinguished. More particularly, the present invention provides a sheathing arrangement to protect an endotracheal tube from being punctured by a laser during surgical procedures where the endotracheal tube includes an inlet to receive anesthesia/oxygen mixture to be supplied to a patient undergoing the surgical procedure and an outlet which extends into the airway of the patent where an expandable seal is provided on the endotracheal tube to seal off the breathing passageway during the procedure and where a second flexible tubular sheath is provided to extend, be sealed around the endotracheal tube adjacent the outlet and extend upwardly substantially the length of endotracheal tube to define an annular area between the tubular sheath and the endotracheal tube where a nonflammable fluid is supplied to the annular area.

Examples of apparatus and method within the scope of the present invention are illustrated in the accompanying drawings and discussed hereinafter but it will be understood that the illustrations and discussions provided herein are by way of example only and that various other arrangements also within the scope of the present invention will occur to those skilled in the art upon reading the disclosures set forth hereinafter.

BRIEF DESCRIPTION OF THE DRAWINGS

Examples and apparatus within the scope of the present invention are illustrated in the accompanying drawings wherein:

FIG. 1 is a partially sectioned view of an endotracheal tube and a device within the scope of the present invention; and FIG. 2 is a perspective view of an example of a sealing useful in a procedure within the scope of the present invention.

DETAILED DESCRIPTION OF THE DRAWINGS

Referring to FIG. 1 an example of a device within the scope of the present invention is illustrated with reference to a standard endotracheal tube 1. For purposes of clarity the tube is shown in sectional form and it will be understood that the tube is normally longer and of smaller diameter. The tube 1 includes an adapter 2 at the inlet to receive a connection for supply of oxygen-/anestestic mixture to the tube. The gas mixture is usually supplied through a breathing circuit of the type commonly known. An outlet 3 is provided having a tapered surface 4 which, as is known in the art, is used to facilitate the insertion and location of the endotracheal tube in the airway of the patient.

An inflatable bladder 6 is provided on the tube 1 and connected by means of tube 7, which is integral with conduit 7A in tube 1, to a connector 8 which has an inlet 9 adapted to receive a supply of pressureized fluid, for example, air, from a syringe to a pilot balloon 16 can be provided to indicate the inflation condition of the balloon 6. A conduit 16A is provided from tube 7 to the pilot balloon so when the pilot balloon is inflated so is the balloon 6. When the endotracheal tube assembly has been inserted into the airway of the patient the anestestia/oxygen mixture is supplied through inlet 2 and out the outlet 3 to sustain the patient and bladder 6 is then expanded in order to seal off the airway of the patient to allow the surgeon to work in the area above the sealed area.

Typically, tube 7 is provided through a conduit 7A in the wall of the tube 1 or a separate tube can be provided within the conduit defined by the tube 1. In any event the tube 7 is connected through outlet 5 with bladder 6 and is utilized to maintain the seal in the throat of the patient.

In assemblies where the arrangement in accordance with the present invention is not used and the anestestia/oxygen mixture is flowing through the tube 1, if the tube is contacted by the laser the heat of combustion of the material of the tube or other means can ignite the tube and anestestia/oxygen mixture causing a fire which usually leads to disaster for the patient.

FIG. 1 illustrates an adaptation in accordance with the present invention which is particularly effective in preventing the occurrence previously described.

Specifically, a tubular sheath 11 is provided and is attached to the tube 1 below the bladder 6. While various means can be provided for attachment, in the arrangement shown the tubular sleeve 11 is placed on the tube 1 from the end 4. A tape 12 is wrapped around the end 13 of the tubular sheath 11 and sheath is then moved longitudinally along the tube 1 to the position shown. In the arrangement shown the sheath has been located below the bladder. An alternative arrangement as shown can be provided where the sheath 13A and tape 12A are located above the bladder.

Prior to insertion of the tubular sheath on the tube 1 a sealing means, in this case a seal ring 14 has been placed on the tube and is held in sealed relation to the tube 1, for example by means of an adhesive. With the end of sheath 14 in place, the tubular sheath 11 is then pulled along the tube and end is fastened to the sheath tube adapter 14, for example by elastomeric band 17. The ring 14 as shown is provided with a passageway 18 by means of a connector 21 to a source of pressurized 23. In the case of gaseous fluid a regulator 22 is provided and connected to a source of pressurized fluid 23.

In accordance with one feature of the present invention the fluid 23 is a nonflammable fluid such as nitrogen, $CO_2$, or other fluids. In accordance with another feature of the present invention even water, or saline solution, can be utilized to fill the annular area 19 between the tubular sheath 11 and the tube 1. Liquid has the benefit of providing a large heat sink to reduce the risk of combustion or penetration by the laser beam.

Thus, in the event the laser is misdirected, it strikes the sheath 11. If the laser punctures the sheath 11 then starts to melt the tube or ignite it, the only harm is the escape of the nonflammable gas, or water, as the case may be, which will extinguish any combustion that might occur at the site. The pressure regulator 22 has been set to maintain a specific pressure in the annular area and thus, the flow increases to accommodate any leakage which may occur as a result of the puncture.

Where saline solution is used a similar arrangement can be provided to supply the solution to the system.

FIG. 2 is a perspective view of an example of the sealing assembly 14 as shown in FIG. 1 in cross section. The sealing element 14, as shown includes an annular surface 14A which is adapted to receive the elastomeric fastener 17 to hold the tubular sheath 11 in sealing relation against the sealing element 14. An inlet 18 is provided as is an outlet 26 from the element 14. As shown an annular groove 27 can be provided around the inner surface of the sealing element 14. Groove 27 is provided to prevent closure of the opening 26 in the event a portion of the sheath material is pressed against the inner surface of the ring. The openings 18 and 26 can be utilized to establish circulation through the annular area 19 if desirable for any reason.

In operation, the element 14 is inserted to specific location on the tube 1. Tubular sheath 11 is then placed over the end 4 of the tube and fastened by means of tape or other similar material 12. The balance of the tube is then turned upwardly over the tube 11 so that the opposite end of the tubular sheath 11 is located over the sealing ring 14 at which time a fastening means 17 is provided to hold the sheath 11 in sealed relation. At this point flow of fluid, for example nonflammable gas or liquid such as saline solution, can be provided from source 23 in order to fill the tubular sheath 11. As shown, where gas is used, a bubbler 33 can be used so bubbles 34 indicate flow of gas through sheath 11 and that there has or has not been a puncture. Where liquid such as saline solution is used a receiver 31 can be provided so that droplets 32 indicate continual flow of liquid and that there has not been a puncture.

It will be understood that the foregoing is but one example of method and apparatus in accordance with the present invention and that various other arrangements also within the scope of the present invention will occur to a person skilled in the art upon reading the disclosure set forth hereinbefore.

The invention claimed is:

1. A fire prevention and suppression assembly for protecting an endotracheal tube of given diameter against being ignited by a laser beam during a surgical procedure, the endotracheal tube including an inlet end portion to receive an anesthesia/oxygen input to be supplied to a patient undergoing the surgical procedure, an outlet end portion insertable into the throat of the patient, and an external, expandable seal cuff on the outlet end portion for sealing off the breathing passageway of the patient during the surgical procedure, the fire prevention and suppression assembly comprising, a flexible tubular sheath, having a diameter substantially larger than said given diameter, encompassing substantially the entire length of the endotracheal tube and enclosing an annular space around the endotracheal tube;

outlet end sealing means sealing the end of the sheath adjacent the outlet end of the endotracheal tube;

inlet end sealing means sealing the end of the sheath adjacent the inlet end of the endotracheal tube, so that the annular space is sealed; and a nonflammable fluid filling the annular space.

2. The fire prevention and suppression assembly for an endotracheal tube according to claim 1 wherein the nonflammable fluid disposed in the annular space is under an increased pressure relative to the ambient environment.

3. The fire prevention and suppression assembly for an endotracheal tube according to claim 2, and further comprising:

a continuous source of nonflammable fluid connected to the annular space between the endotracheal tube and the tubular sheath; and a pressure regulator disposed between the source of nonflammable fluid and the annular space for regulating and maintaining the pressure at a level slightly above the ambient environment.

4. The fire prevention and suppression assembly for an endotracheal tube according to claim 1 wherein the nonflammable fluid comprises a fluid.

5. The fire prevention and suppression assembly for an endotracheal tube according to claim 4 wherein the liquid is provided within the annular space in sufficient volume to constitute a heat sink in the event that a laser beam accidentally strikes the sheath during the surgical procedure on the patient.

6. The fire prevention and suppression assembly for an endotracheal tube according to claim 4 wherein the liquid comprises water.

7. The fire prevention and suppression assembly for an endotracheal tube according to claim 4 wherein the liquid comprises a saline solution.

8. The fire prevention and suppression assembly for an endotracheal tube according to claim 2 wherein the nonflammable fluid comprises a gas.

9. The fire prevention and suppression assembly for an endotracheal tube according to claim 8 wherein the gas is from the group consisting of nitrogen and carbon dioxide.

10. The fire prevention and suppression assembly for an endotracheal tube according to claim 1 wherein the tubular sheath substantially surrounds the expandable airway seal to protect the seal from being ignited by a laser beam.

* * * * *